US008992553B2

(12) United States Patent
Diamant et al.

(10) Patent No.: US 8,992,553 B2
(45) Date of Patent: Mar. 31, 2015

(54) CUTTING BALLOON ASSEMBLY AND METHOD OF MANUFACTURING THEREOF

(75) Inventors: Valery Diamant, Katzrin (IL); Haim Danenberg, Jerusalem (IL); Chaim Lotan, Jerusalem (IL); Nadezda Yasko, Tomsk (RU)

(73) Assignee: Cardioniti, Katsrin (IL)

( * ) Notice: Subject to any disclaimer, the term of this patent is extended or adjusted under 35 U.S.C. 154(b) by 0 days.

(21) Appl. No.: 12/571,557

(22) Filed: Oct. 1, 2009

(65) Prior Publication Data
US 2011/0082483 A1   Apr. 7, 2011

(51) Int. Cl.
| A61B 17/22 | (2006.01) |
| A61B 17/3207 | (2006.01) |
| A61B 19/00 | (2006.01) |
| A61B 17/00 | (2006.01) |
| A61F 2/958 | (2013.01) |

(Continued)

(52) U.S. Cl.
CPC ..... *A61B 17/22032* (2013.01); *Y10T 29/49826* (2015.01); *A61B 17/320725* (2013.01); *A61B 19/54* (2013.01); *A61B 2017/00526* (2013.01); *A61B 2017/00539* (2013.01); *A61B 2017/00853* (2013.01); *A61B 2017/00893* (2013.01); *A61B 2017/22061* (2013.01); *A61F 2/958* (2013.01); *A61M 25/0045* (2013.01); *A61M 25/0053* (2013.01); *A61M 25/1034* (2013.01); *A61M 25/104* (2013.01); *A61M 2025/0057* (2013.01); *A61M 2025/105* (2013.01)
USPC ............................. 606/159; 606/192; 606/194

(58) Field of Classification Search
CPC ................. A61B 17/22032; A61B 17/320725
USPC ............. 606/159, 191, 192, 194; 604/103.08, 604/103.09; 623/1.13, 1.23
See application file for complete search history.

(56) References Cited

U.S. PATENT DOCUMENTS

| 4,619,261 A | * | 10/1986 | Guerriero ..................... 606/194 |
| 5,102,390 A | * | 4/1992 | Crittenden et al. ........... 606/192 |
| 5,196,024 A | | 3/1993 | Barath |

(Continued)

FOREIGN PATENT DOCUMENTS

| RU | 2093087 C1 | 10/1997 |
| RU | 2380054 C2 | 1/2010 |

(Continued)

OTHER PUBLICATIONS

International Search Report mailed Nov. 29, 2010 from PCT/IL2010/000604 filed Jul. 28, 2010.

(Continued)

*Primary Examiner* — Kathleen Holwerda
*Assistant Examiner* — Sarah W Aleman
(74) *Attorney, Agent, or Firm* — Oliff PLC

(57) ABSTRACT

A cutting balloon assembly and a method for fabrication of the assembly is described. The cutting balloon assembly comprises a delivery catheter, an expandable balloon mounted on the catheter distal end, and a scoring mesh disposed around the expandable balloon. The scoring mesh comprises interlacing filaments that extend from a mesh proximal end towards a mesh distal end, form distal filament loops at said mesh distal end, and then return to the mesh proximal end. At least a part of the interlacing filaments forms one or more permanent links with neighboring filaments between the mesh proximal end and the mesh distal end.

21 Claims, 10 Drawing Sheets

(51) Int. Cl.
*A61M 25/00* (2006.01)
*A61M 25/10* (2013.01)

(56) References Cited

U.S. PATENT DOCUMENTS

| | | | |
|---|---|---|---|
| 5,800,519 A | 9/1998 | Sandock | |
| 6,241,757 B1 * | 6/2001 | An et al. | 623/1.1 |
| 6,547,819 B2 * | 4/2003 | Strecker | 623/1.22 |
| 7,101,392 B2 | 9/2006 | Heath | |
| 7,291,158 B2 | 11/2007 | Crow et al. | |
| 7,435,254 B2 * | 10/2008 | Chouinard et al. | 623/1.35 |
| 7,655,039 B2 * | 2/2010 | Leanna et al. | 623/1.53 |
| 2004/0243156 A1 | 12/2004 | Wu et al. | |
| 2006/0259005 A1 | 11/2006 | Konstantino et al. | |
| 2006/0271093 A1 * | 11/2006 | Holman et al. | 606/194 |
| 2007/0198047 A1 | 8/2007 | Schon et al. | |
| 2008/0183132 A1 * | 7/2008 | Davies et al. | 604/103.09 |
| 2008/0275542 A1 * | 11/2008 | LaDuca et al. | 623/1.35 |
| 2009/0099640 A1 * | 4/2009 | Weng | 623/1.11 |
| 2009/0240270 A1 * | 9/2009 | Schneider et al. | 606/159 |
| 2010/0023047 A1 * | 1/2010 | Simpson | 606/192 |
| 2010/0042121 A1 * | 2/2010 | Schneider et al. | 606/159 |
| 2010/0234875 A1 | 9/2010 | Allex et al. | |

FOREIGN PATENT DOCUMENTS

| | | |
|---|---|---|
| WO | 9732546 A1 | 9/1997 |
| WO | 9949812 A2 | 10/1999 |

OTHER PUBLICATIONS

Sep. 16, 2013 Office Action issued in U.S. Appl. No. 13/478,242.

* cited by examiner

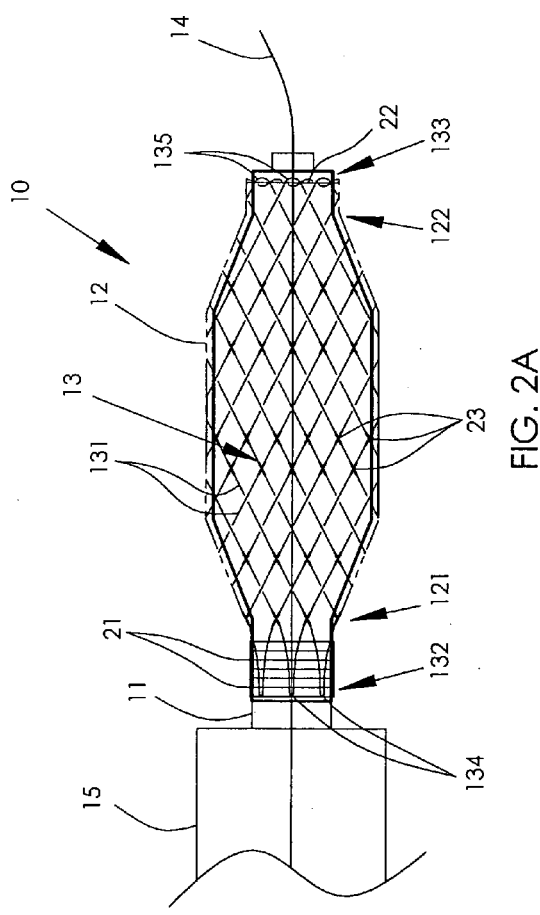
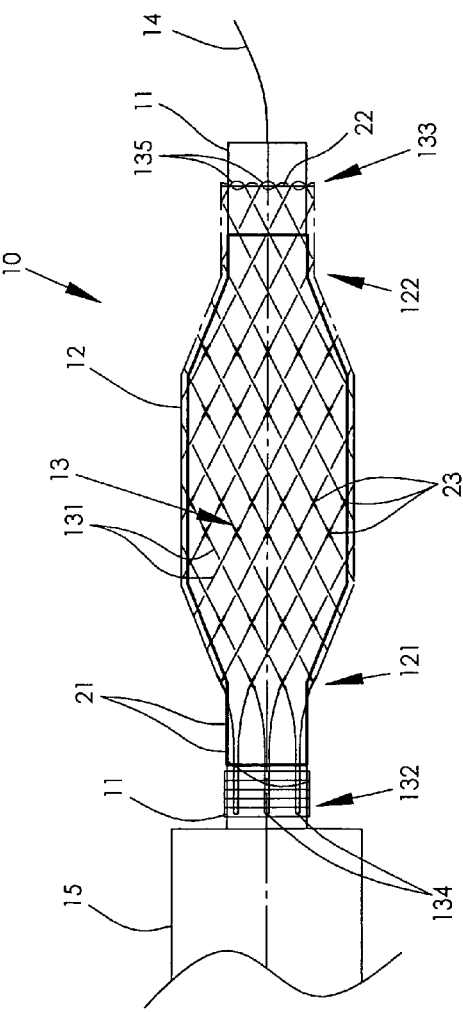
FIG. 2A
FIG. 2B

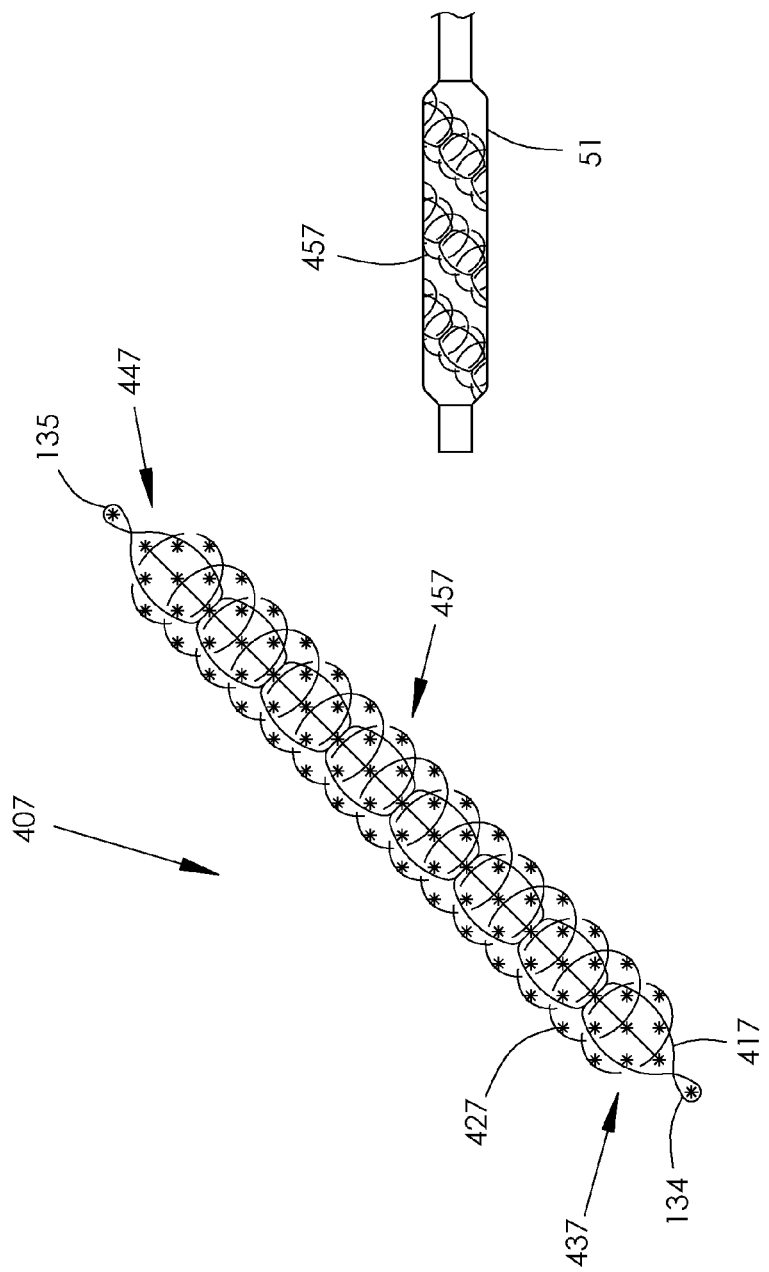

CUTTING BALLOON ASSEMBLY AND METHOD OF MANUFACTURING THEREOF

FIELD OF THE INVENTION

This invention relates generally to medical devices and more particularly to angioplasty balloon devices for expanding passageways in the venous system.

BACKGROUND OF THE INVENTION

One of the most common heart diseases is atherosclerotic cardiovascular disease, caused by the buildup of lesions or plaque on the inside wall of blood vessels. For example, a variety of lesions may occur related to atherosclerosis, including aorto-ostial lesions. Aorto-ostial lesions damage the ostium of the main blood vessels branching from the aorta. This can result in a partial, or even complete, blockage of the artery. As a result of the danger associated with such a blockage, several methods and procedures have been developed to treat arterial blockages.

One such method is an angioplasty procedure which uses an inflatable balloon to dilate the blocked artery. Angioplasty procedure involves the use of a dilatation balloon catheter. The balloon catheter is advanced, using fluoroscopy, over a guidewire so that the balloon is positioned adjacent a stenotic lesion. The balloon is then inflated inside a stenosed region in a blood vessel in order to apply radial pressure to the inner wall of the vessel and widen the stenosed region to enable better blood flow.

The efficacy of the dilation of a stenosis can be enhanced by incising the material that creates the stenosis. Consequently, angioplasty balloons with scoring elements, such us cutting edges, atherotomes or blades mounted on the surface of the balloon were proposed, which are intended to incise a stenosis during the dilation procedure. The cutting balloons can also be used to break through or scrape plaque and stenoses.

For example, U.S. Pat. No. 5,196,024 to Barath et al. describes a device and method for dilation or recanalization of a diseased vessel by use of a balloon catheter with cutting edges to make longitudinal cuts in the vessel wall. The diameter of the vessel can be increased without subsequent secondary cellular proliferation or restenosis in the vessel caused by angioplasty methods.

U.S. Pat. Pub. No. 2004243156A to Show-men et al. and U.S. Pat. No. 7,291,158 to Bence et al. describe various angioplasty balloon catheters and methods of making and using the same. The balloon catheters include a catheter shaft and a balloon coupled to the shaft. The balloon catheters include one or more cutting edges, blades or wings coupled to the balloon.

One of the drawbacks of the prior art cutting balloons equipped with cutting edges or blades is associated with the fact that these devices tend to be fairly stiff. This has the affect of limiting the flexibility and deliverability of the balloon as it is advanced through the tortuous confines of a vessel or other body lumens. Moreover, the cutting balloons equipped with cutting blades and edges can be difficult to deflate and collapse. This can make removal of the balloons from the vasculature more difficult than the removal of corresponding angioplasty balloons which do not include stiff cutting blades. Additionally, it was found that the cuts imparted by such cutting balloons do not always provide the dilatation and treatment of fibrotic lesions as would be desired.

Angioplastic balloons that employ a woven mesh, cutting strings or wires are also known. These balloons are proved to be more flexible and safer than the balloons employing cutting blades and edges.

For example, U.S. Pat. Pub. No. 2006/259005A describes an angioplasty dilatation device provided with scoring elements which may incorporate a drug to be delivered to a body lumen, typically a blood vessel. The scoring elements can, for example, be in the form of a single wire or a plurality of wires wrapped around a dilatation balloon in a helical configuration.

U.S. Pat. Pub. No. 2007/198047A describes a cutting balloon catheter assembly including a catheter equipped with an inflatable balloon having an interior cavity and an expandable covering disposed about the balloon. The expandable covering is in the form of a mesh coating having a cross-hatched pattern. The mesh coating is made of plastic or metal fibers, where some of the fibers have cutting edges. In operation, the cutting edges abrade the stenoses, plaque or lesions along the vessel walls, when the catheter assembly is reciprocally moved longitudinally or rotationally after inflation of the balloon.

A coronary stenting procedure is known in the art for treatment of aorto-ostial lesions. An incomplete apposition between the stent filaments and the arterial wall can increase the risk of an embolic source as a result of the stagnation of the blood flow in the dead space. A strong compression of the vessel wall on the opposite side of the unattachment at the stent edge because of the straightening effect on tortuous vascular curves may induce a kink in the artery that thus could possibly cause edge restenosis. It is also recognized in the art that incomplete expansion of the stent as compared with a predefined reference (stent underexpansion) can result in calcification, which significantly increases the subsequent risks of restenosis and/or stent thrombosis.

Systems and methods are known that provide stent visualization in coronary arteries, and provide analysis tools based on enhanced angiograms (of the deployed stent). Such analysis can provide information on the success of the stent deployment. Based on the enhanced image the physician can decide whether the procedure was carried out satisfactory or might also decide to further dilate or deploy another stent. The shortcoming of all those systems and methods is that they are providing information only after stent deployment.

SUMMARY OF THE INVENTION

There is a need in the art to provide a cutting balloon assembly that will be more flexible, safer and provide improved dilatation and treatment of fibrotic lesions.

It would be advantageous to have a cutting balloon assembly equipped with such a scoring mesh that does not prevent inflation of the balloon and that returns to its original state after deflation of the balloon.

It would be beneficial when a scoring mesh and clamps fastening the mesh to the delivering catheter or expandable balloon would have flexibility sufficient for the cutting balloon assembly to pass through the tortuous confines of a vessel or other body lumens and do not damage them.

It would also be advantageous to have a scoring mesh made of filaments having such a dimension and a shape of the cross-section so as to incise calcified, fibrotic and other hard stenosed region and to leave scores and grooves thereon during the dilation procedure. Such grooves may facilitate a further positioning of a stent at the scored place.

It would also be beneficial to have a cutting balloon assembly such that it can a score a relatively large area that may allow the deposition of a large amount of drugs in the scores.

It would further be advantageous to have a cutting balloon assembly comprising a scoring mesh built up of drug-eluting filaments to allow controlled local release of a drug directly to the injured endothelium, thereby avoiding side effects, such as restenosis.

There is also a need for a device and method that could provide indications and analysis for a sub-optimal deployment before the stent is delivered and deployed. This could assist the physician in selection of the best treatment and deployment strategy.

Thus, it would be beneficial to have a scoring mesh radiopaque, so as to permit it to be visualized by a fluoroscope during use in anatomy. The radioopaque scoring mesh can also provide a simulation of a possible deployed stent, thus providing a possibility for analysis of sub-optional deployment.

It would further be advantageous to have a scoring mesh which is symmetrical. This feature would enable the operator to maintain the symmetry of the mesh pattern visualized by a fluoroscope during angioplasty procedure in order to control the treatment of plaque or stenosis and predict how a stent will further be positioned after removal of the cutting balloon catheter from the treated vessel. The distortion of the symmetry of the mesh pattern visualized by a fluoroscope may indicate the undulations of the inner surface of the vessel and the quality of the angioplasty treatment.

The present invention satisfies the aforementioned needs by providing a novel cutting balloon assembly. The cutting balloon assembly includes a delivery catheter having a catheter proximal end, a catheter distal end, and at least one catheter lumen extending between the catheter proximal and distal ends. The assembly includes also an expandable balloon having a balloon proximal end and a balloon distal end. The expandable balloon is mounted on the catheter distal end. The assembly further includes a scoring mesh disposed around the expandable balloon. The scoring mesh comprises interlacing filaments that interweave between a mesh proximal end and a mesh distal end. At least a part of the interweaving filaments intertwines to form at least one permanent link with neighboring filaments. It should be noted that the expression "interlacing", as used for the purpose of the present description, has a general meaning that includes "interweaving" and "intertwining". The expression "interweaving" for filaments implies passing each of the filaments above one or more other filaments and under one or more other filaments, whereas the expression "intertwining" for filaments implies uniting the filaments by twining one filament with another (e.g., twisting the filaments together by one or more turns) and/or twining one filament about another. Thus, due to the intertwining, at least a part of the interlacing filaments can form at least one permanent link with neighboring filaments between the mesh proximal end and the mesh distal end.

According to one embodiment of the present invention, the interlacing filaments form at least distal filament loops at the mesh distal end. According to another embodiment of the present invention, the interlacing filaments form the distal filament loops at the mesh distal end along with proximal filament loops at a mesh proximal end.

The scoring mesh is connected to the balloon proximal and distal ends. According to one embodiment, the cutting balloon assembly comprises one or more distal strings that are wound round the balloon distal end. The distal strings pass through openings in the distal filament loops, thereby to tie the distal filament loops of the scoring mesh to the balloon distal end.

When the interlacing filaments form also the proximal filament loops at the mesh proximal end, the cutting balloon assembly can comprise one or more proximal strings wound round the balloon proximal end. The proximal strings pass through the openings in the proximal filament loops, thereby to tie the proximal filament loops of the scoring mesh to the balloon proximal end.

According to a further embodiment, the cutting balloon assembly can comprise one or more distal strings wound round the delivery catheter after the balloon distal end in relation to an operator using the cutting balloon assembly. The distal string can pass through the openings in the distal filaments loops, thereby to tie the scoring mesh to the delivery catheter.

According to yet an embodiment, the cutting balloon assembly can comprise one or more proximal strings wound round the delivery catheter before the balloon proximal end in relation to an operator using the cutting balloon assembly, thereby to tie the filaments at the mesh proximal end to said delivery catheter.

According to an embodiment, the scoring mesh includes scoring elements. The scoring elements can, for example, be formed by twisted turns of the entwined filaments. Likewise, the scoring elements can be certain dedicated elements attached to or placed around the filaments forming the scoring mesh.

According to an embodiment, the interlacing filaments of the scoring mesh are radiopaque. The radioopaque scoring mesh can also provide a simulation of a possible deployed stent, thus providing a possibility for analysis of sub-optional stent deployment.

According to an embodiment, at least a part of the scoring mesh comprises an active pharmacological agent that can inhibit inflammation and smooth-muscle cell growth.

The cutting balloon assembly can comprise a guiding catheter that includes a lumen for housing the delivery catheter. The lumen has sufficient size for receiving the distal end of the delivery catheter therethrough together with the locator unit in a contracted condition.

The cutting balloon can be equipped with one or more guide wires.

The present invention also satisfies the aforementioned needs by providing a method for fabrication of the cutting balloon assembly described above. The method comprises providing a predetermined number of filaments having predetermined properties, diameter and length and fabricating a scoring mesh from these filaments. The fabrication of the scoring mesh includes providing a weaving jig having a cylindrical structure including a plurality of pins disposed circumferentially about the surface of the structure in rows and extending outwardly therefrom. The filaments are placed between the pins and interlaced (i.e., interweaved and intertwined) with neighboring filaments to form a scoring mesh. The interlacing of the filaments includes interweaving the filaments between the mesh proximal end and the mesh distal end, and intertwining at least a part of the interlacing filaments to form one or more permanent links with neighboring filaments. The permanent links can be formed by twining one filament with another (i.e., twisting the filaments together by one or more turns) and/or twining one filament about another.

The fabrication of the scoring mesh also includes forming distal filament loops at least at the mesh distal end. When desired, proximal filament loops can also be formed at the mesh proximal end.

The fabrication of the scoring mesh further includes annealing the scoring mesh.

According to one embodiment, the fabricating of the scoring mesh includes providing scoring elements on the filaments forming the scoring mesh.

According to one embodiment, the fabricating of the scoring mesh further includes providing an active pharmacologic agent within the scoring mesh. The providing of the active pharmacologic agent can include coating at least a portion of a surface of the filaments with a material including such an agent.

The fabrication of the cutting balloon assembly further includes providing a delivery catheter. The delivery catheter has a catheter proximal end, a catheter distal end, and at least one catheter lumen extending between the catheter proximal and distal ends. The fabrication of the cutting balloon assembly also includes providing an expandable balloon having a balloon proximal end and a balloon distal end. The expandable balloon is mounted on the catheter distal end. The fabrication of the cutting balloon assembly also includes mounting the scoring mesh prepared as described above on the expandable balloon.

According to one embodiment, the mounting of the scoring mesh on the expandable balloon includes connecting the scoring mesh to the balloon proximal and distal ends. The scoring mesh can be connected to the delivery catheter after the balloon distal end and before the balloon proximal end in relation to an operator using the cutting balloon assembly.

For example, the mounting of the scoring mesh on the expandable balloon can include winding at least one distal string around the balloon distal end and passing through openings in the distal filament loops, thereby to tie the distal filament loops of the scoring mesh to the balloon distal end. Likewise, the mounting of the scoring mesh on the expandable balloon can include winding at least one proximal string around the balloon proximal end and passing through the openings in the proximal filament loops, thereby to tie the proximal filament loops of the scoring mesh to the balloon proximal end.

According to still another aspect of the present invention, there is provided a method for a simulation of an optimal position for deployment of a stent. The method includes providing a balloon assembly described above, in which the filaments of the scoring mesh are radiopaque. This balloon assembly is advanced, by using fluoroscopy, over a guidewire within the cardiovascular system of a patient so that to place the balloon adjacent a stenotic lesion inside a stenosed region. Then, the balloon is inflated and angiograms of the radioopaque scoring mesh are taken. Further, the method includes processing and analyzing an image of the radioopaque scoring mesh on the angiograms so as to obtain the optimal position for deployment of the stent.

There has thus been outlined, rather broadly, the more important features of the invention in order that the detailed description thereof that follows hereinafter may be better understood. Additional details and advantages of the invention will be set forth in the detailed description, and in part will be appreciated from the description, or may be learned by practice of the invention.

BRIEF DESCRIPTION OF THE DRAWINGS

In order to understand the invention and to see how it may be carried out in practice, embodiments will now be described, by way of non-limiting example only, with reference to the accompanying drawings, in which:

FIGS. 2A-B illustrate schematic longitudinal fragmentary views of the distal portion of the cutting balloon assembly shown in FIG. 1, according to two embodiments of the present invention;

FIGS. 4A-4G show various embodiments of the pattern of the scoring mesh of the present invention; and FIG. 5 illustrates a schematic longitudinal fragmentary view of the distal portion of the cutting balloon assembly shown in FIG. 1, according to a further embodiment of the present invention.

DETAILED DESCRIPTION OF THE PREFERRED EMBODIMENTS

Figure 1:
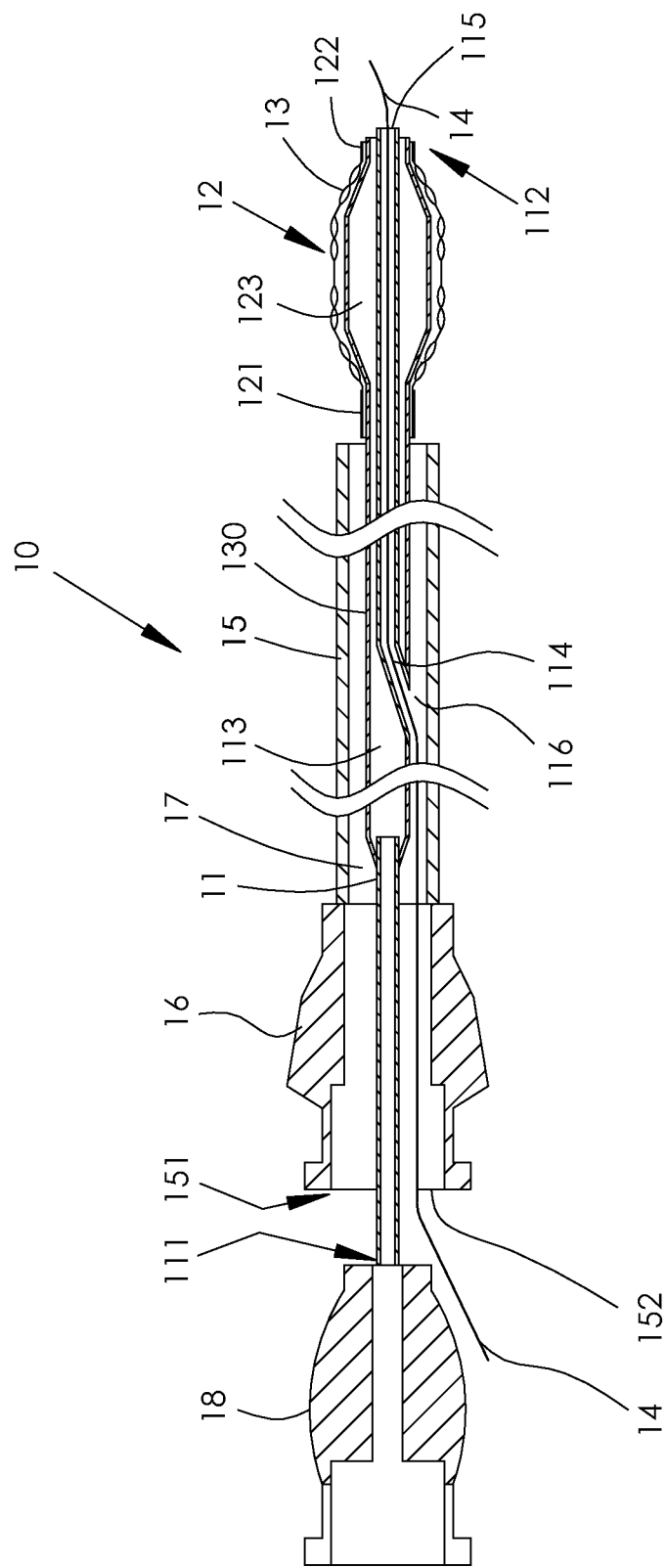
FIG. 1 illustrates a schematic longitudinal cross-sectional view of a cutting balloon assembly, according to one embodiment of the present invention.

The principles of the medical device according to the present invention may be better understood with reference to the drawings and the accompanying description, wherein like reference numerals have been used throughout to designate identical elements. It being understood that these drawings which are not necessarily to scale, are given for illustrative purposes only and are not intended to limit the scope of the invention. Examples of constructions, materials, dimensions, and manufacturing processes are provided for selected elements. Those versed in the art should appreciate that many of the examples provided have suitable alternatives which may be utilized. Certain terminology is used herein for convenience only and is not to be taken as a limitation on the present invention. As used throughout this description, proximal and distal orientation relationships are in relation to an operator (e.g., interventional cardiologist/radiologist) utilizing the invention as described herein.

Referring to FIG. 1, a schematic longitudinal cross-sectional view of a distal portion of a cutting balloon assembly 10 is illustrated, according to one embodiment of the present invention. It should be understood that the cutting balloon assembly 10 is not bound to the scale and proportion illustrated in FIG. 1 and in other drawings. The cutting balloon assembly 10 is used to expand passageways in a patient's blood vessel (not shown) by cutting blockages within the vessel. A blockage may be a lesion, stenosis, plaque or any other infliction that would constrict a patient's vessel.

Generally, the cutting balloon assembly 10 includes a delivery catheter 11, an expandable balloon 12, and a scoring mesh 13 disposed around the expandable balloon 12. The delivery catheter 11 is in the form of an elongate tubular member and has a catheter proximal end 111, a catheter distal end 112, and one or more catheter lumens 113 and 114 extending between the catheter proximal and distal ends. According to the embodiment shown in FIG. 1, the delivery catheter 11 has an axial lumen 114 located along a longitudinal axis (not indicated) of the delivery catheter 11, and an exterior (or inflation/deflation) lumen 113 located about the axial lumen 114. The axial lumen 114 is sized to accommodate a guidewire 14 that can be inserted therethrough along the longitudinal axis of the delivery catheter 11. The inflation/deflation lumen 113 is used to establish fluid communication between the expandable balloon and external balloon inflation device (not shown). It should be noted that although FIG. 1 shows a coaxial arrangements of wire guide lumen 114 and the inflation/deflation lumen 113, when desired, the lumen for receiving a guidewire and the inflation/deflation lumen can be both positioned side-by-side within the delivery catheter, mutatis mutandis.

The delivery catheter 11 is a deflectable tube fabricated of a relatively stiff yet somewhat pliant material, which permits the device to be introduced into a patient's vascular system along a tortuous path. The delivery catheter 11 can be formed from plastic, metal, or composite materials, e.g., a plastic material having a wire, braid, or coil core, which may prevent kinking or buckling of the delivery catheter 11 during advancement. Examples of materials suitable for the delivery catheter 11 include, but are not limited to, polyurethane, polyimide, nylon, polyester or some other suitable biocompatible material.

The expandable balloon 12 is located at the catheter distal end 112 and has a balloon proximal end 121, a balloon distal end 122, and an interior cavity 123 located between the balloon proximal end 121 and the balloon distal end 122. As shown in FIG. 1, the expandable balloon 12 is disposed circumferentially about the delivery catheter 11 at the distal end 112. The expandable balloon 12 is fixedly attached to the exterior wall of the delivery catheter 11, by bonding, adhesion, ultrasonic welding or any other suitable attachment technique to form a liquid-tight seal and communication between the balloon 12 and the exterior lumen 113 of the catheter 130. The expandable balloon 12 can, for example, be constructed from polyurethane, silicone or some other suitable biocompatible material. A diameter of the balloon 12 can, for example, be from about 4 to about 20 mm for use in the venous system, and from about 1.5 to about 12 mm for use in the arterial system.

The cutting balloon assembly 10 can also include a guiding catheter 15 and a manipulator 16 of the guiding catheter 15. The guiding catheter 15 of the cutting balloon assembly 10 can be in the form of a thin-walled, cylindrical flexible tube adapted to penetrate into a body passage (not shown) to reach the location of plaque or stenosis under treatment. The delivery catheter 11 is mounted within the guiding catheter 15, and can be manipulated by the operator from the outside at the guiding catheter's proximal end 151.

The guiding catheter 15 may be constructed from substantially flexible, durable, strong and/or floppy materials. For example, the guiding catheter 15 can be made of a flexible, durable, strong plastic material and/or plastic having a braid or other reinforcement (not shown) that sufficiently supports the guiding catheter 15 to prevent kinking or buckling, while allowing the guiding catheter 15 to be directed easily through tortuous vessel ducts. Examples of such plastic include, but are not limited to, polyimide, polyvinyl chloride, nylon, teflon, etc. The guiding catheter 15 can also be made of a composite material, such as a wire mesh or a coil, (e.g., stainless steel coil). When desired, the guiding catheter 15 may be multi-layered with different materials in order to provide a graduated bending and stiffness characteristic over its length.

The guiding catheter 15 includes a lumen 17 for housing the delivery catheter 11. The lumen 17 has sufficient size for receiving the distal end 112 of the delivery catheter 11 therethrough together with the expandable balloon 12 in the deflated condition.

The cutting balloon assembly 10 may include a handle 18 on the catheter proximal end 111 to facilitate manipulating the delivery catheter 11. When desired, the handle 18 can be integrated with the manipulator 16 for manipulating the cutting balloon assembly 10 for delivering the scoring mesh 13.

As shown in FIG. 1, the cutting balloon assembly 10 can be equipped with a guide wire 14 that extends from a guide wire port 116 of the delivery catheter 11 through the lumen 111 to an opening 115 arranged in a distal tip of the catheter distal end 112. As shown in FIG. 1, the guide wire 14 also extends through the lumen 17 of the guiding catheter 15 and passes through a guide wire port 152 arranged in the manipulator 16.

Referring to FIG. 2A, the scoring mesh 13 is disposed around the expandable balloon 12 between the balloon proximal end 121 and the balloon distal end 122 and covers the expandable balloon 12. The scoring mesh 13 includes interlacing filaments 131 that interweave between a mesh proximal end 132 and a mesh distal end 133 and have a crosshatched pattern. As a result of the interweaving, each of the filaments passes above one or more other filaments and then under one or more other filaments, and vice versa.

According to an embodiment, the interlacing filaments 131 form one or more permanent links with neighboring filaments between the mesh proximal end and the mesh distal end. The permanent links are formed by intertwining a part of the filaments interweaving between the mesh proximal end and the mesh distal end. The intertwining can, for example, be carried out by twisting one filament with another by one or more turns and/or by twining one filament about another.

A concentration of the permanent links within the permanent links determines a strength and flexibility of the mesh. Moreover, the permanent links formed among the intertwining filaments 131 can maintain the symmetry of the mesh pattern during the angioplasty procedure, since the permanent links can prevent the slippage of the filaments away from their original contact points. The symmetry of the mesh pattern can be visualized by a fluoroscope during angioplasty procedure so as to control the treatment of plaque or stenosis and predict how a stent will further be positioned after removal of the cutting balloon catheter from the treated vessel. The distortion of the symmetry of the mesh pattern visualized by a fluoroscope may indicate, inter alia, the undulations of the inner surface of the vessel and the quality of the angioplasty treatment.

According to one embodiment, the interlacing filaments 131 form proximal filament loops 134 at least at the mesh proximal end 132. According to another embodiment, the interlacing filaments 131 form proximal filament loops 134 at least at the mesh proximal end 132 along with distal filament loops 135 at the mesh distal end 133. It should be noted that provision of filament loops at the mesh proximal and distal ends makes the scoring mesh 13 less traumatic to the soft tissues of blood vessels than sharp ends of single wires. Moreover, as will be described below, the loops can facilitate attaching of the scoring mesh 13 to the cutting balloon assembly 10.

The scoring mesh 13 can be connected to the ends of the expandable balloon 12 or to the delivery catheter 11 at one or more points.

According to one embodiment, the scoring mesh 13 is connected to the proximal and distal ends 121 and 122 of the expandable balloon 12. Specifically, the proximal filament loops 134 located at the mesh proximal end 132 can be tied to the balloon proximal end 121, whereas the distal filament loops 135 located at the mesh distal end 133 can be tied to the balloon distal end 122. The loops 134 and 135 can be tied by one or more proximal strings 21 and distal strings 22 wound round the balloon proximal and distal ends 121 and 122, and passing through openings in the loops 134 and 135, correspondingly. Examples of the strings suitable for fastening the loops include, but are not limited to, cotton yarn 10-0 and/or stainless cord having a diameter in the range of about 0.025 mm to 0.075 mm.

Moreover, a medically-acceptable adhesive may also be used to secure or connect the filament loops 134 and 135 of the scoring mesh 13 to the balloon proximal and distal ends 121 and 122, correspondingly. Examples of such an adhesive include, but are not limited to, LOCTITE® 4011 cyanoacrylate and LOCTITE® M-31CLT™ Hysol® Medical Device Epoxy Adhesive.

According to another embodiment, the mesh proximal end 132 can be located on the delivery catheter 11 before the balloon proximal end 121, whereas the mesh distal end 133 can be located on the delivery catheter 11 after the balloon distal end 122, in relation to an operator using the cutting balloon assembly 10. In this case, the scoring mesh 13 can be connected to the surface circumference of the delivery catheter 11 at the mesh proximal end 132 and the mesh distal end 133 (FIG. 2B).

The scoring mesh 13 can be tied to the delivery catheter 11 at the mesh proximal end 132 before the balloon proximal end 121 in relation to an operator using the cutting balloon assembly 10 by one or more proximal strings 21 wound round the delivery catheter and passing through openings of the loops 134. Likewise, the scoring mesh 13 can be tied to the delivery catheter 11 at the mesh distal end 133 after the balloon distal end 122 in relation to an operator using the cutting balloon assembly 10 by at least one distal string 22 wound round the delivery catheter and passing through openings of the loops 135. Moreover, a medically-acceptable adhesive may also be used to secure or connect the filament loops 134 and 135 of the scoring mesh 13 to the delivery catheter 11. Alternatively, the filament loops 134 and 135 of the scoring mesh 13 can be soldered, brazed or welded to the delivery catheter 11 at the joining portions before the balloon proximal end 121 and after the balloon distal end 122.

In operation, the scoring mesh 13 does not prevent inflation of the balloon and can return to its original state after deflation of the balloon 12. The scoring mesh 13 and the regions in which the mesh is connected to the delivery catheter 11 may have flexibility sufficient for the cutting balloon catheter 10 to pass through the tortuous confines of a vessel or other body lumens and do not damage them.

When desired, the filaments 131 of the scoring mesh 13 can have a dimension and shape of the cross-section so as to incise a calcinated and other hard stenosed region and to leave scores and grooves thereon during the dilation procedure. Such grooves may facilitate a further positioning of a stent at the scored place. For example, the filaments 131 can each have a cross-sectional dimension in the range of about 0.01 mm to about 0.5 mm, and preferably in the range of 0.05 mm to 0.2 mm. The cross-sectional shape and dimension of the filaments may vary from wire-to-wire and/or along the lengths of each wire. The cross-section of at least a part of the filaments can, for example, have a circular shape, oval shape, D-shape, rectangular shape, polygonal or any other appropriate shape that can provide rather sharp edges that can incise calcinated and other hard stenosed regions of the patient's blood vessel and to leave scores and grooves on the regions during the dilation procedure. The outer periphery of the filaments may be formed with a centerless grinding process, laser cutting or by another suitable method to provide a smooth profile, and desired shapes, tapers and changes in dimension.

According to a further embodiment, the scoring mesh 13 can include scoring elements 23. The scoring elements 23 can, for example be formed by turns of the entwined filaments forming permanent links. Due to aggregation of two filaments together, these turns on a short piece of length have a dimension that distinguishes from the dimension of a single wire filament, and thereby they have scoring properties.

Likewise, scoring elements 23 can be dedicated elements attached to or placed around the filaments forming the scoring mesh 13. Examples of the dedicated elements forming the scoring elements include, but are not limited to, ferrules with cutting edges placed around the filaments and blades attached to the filaments. As shown in FIGS. 2A-B, the dedicated scoring elements 23 can, for example, be mounted in points of intersection of the filaments, however other locations are also contemplated.

In operation, the scoring elements 23 can incise a calcinated and other hard stenosed region and leave scores and grooves thereon during the dilation procedure. Such grooves may facilitate a further positioning of a stent at the scored place.

The filaments utilized for the fabrication of the scoring mesh 13 can be made of a material that is suitably biocompatible. Moreover, the filaments utilized for the fabrication of the scoring mesh 13 can have thermo-mechanical shape memory and/or superelastic properties.

According to one embodiment of the invention, the filaments utilized for the scoring mesh 13 are made of a metallic material. For example, the metallic material can be selected from a NiTi based alloy (e.g., Nitinol), stainless steel and other materials possessing good shape memory, elastic or superelastic characteristics. According to another embodiment of the invention, the filaments are made of non-metallic materials, e.g. Capron, Nylon, etc.

According to a further embodiment of the invention, the filaments of the scoring mesh 13 are covered by an insulating layer. The insulating layer can, for example, be made of Teflon. The advantage of Teflon is its thermal resistance and low coefficient of mechanical friction, which leads to an additional reduction of traumatism.

Preferably, the filaments are radiopaque, so as to permit them to be visualized by a fluoroscope with respect to a stenosed region in a blood vessel. Thus, according to one embodiment, in order to provide radiopacity, the metallic material from which the filaments are made can include a material which provides radiopacity, e.g., a noble metal, such as gold (Au), tantalum (Ta), platinum (Pt), etc. Likewise, the metallic material can be alloyed with one or more metals selected from Pd, W, Nb, Co, Cu, etc.

According to another example, the filaments are made of a core tube (cannular strand) containing an axially disposed radiopaque material.

According to yet another example, the filaments can have radiopaque parts of a predetermined length. These radiopaque filament parts can form at least a portion of the scoring mesh 13.

Radiopacity can also be improved through coating processes such as sputtering or plating a radiopaque material onto the filaments, or the scoring mesh 13 fabricated from these filaments, thereby to provide a radiopaque coating layer on the filaments.

Likewise, radiopacity can yet be improved by using radiopaque markers (not shown) which can be attached to or placed around the filaments forming the scoring mesh 13. In this manner, materials which have higher radiopacity than the mesh structure itself, such as gold, tantalum or platinum, can be utilized as markers and be strategically placed along the body of the mesh to increase its visualization. For example, the scoring mesh 13 can comprise one or more radiopaque markers (not shown) attached to or placed around the filaments along the mesh length. For example, the radiopaque marker can be a ferrule put on the filament.

According to yet an embodiment of the invention, the filaments of the scoring mesh can include radiopaque coils having the predetermined length, which are put on a core wire in the desired locations along the wire length. In order to avoid slippage of the coils along the core wire, the coils can be welded, soldered and/or glued to the wire. Other methods of binding the coils to the core wire can also be utilized.

According to still another embodiment of the invention, the filaments can be multi-wire strands. In such a case, in order to improve radiopacity, the multi-wire strands can include a central core wire and at least one another wire twisted about said central core wire which is made of a material having a level of radiopacity greater than the level of radiopacity of said central core wire. Examples of such a material include, but are not limited to, gold (Au), tantalum (Ta), platinum (Pt), etc.

The radioopaque scoring mesh can also provide a simulation of a possible deployed stent, thus providing a possibility for analysis of sub-optional deployment. In practice, once the balloon is inflated within the cardiovascular system of a patient, the radio opaque scoring mesh angiograms are taken. The mesh can simulate a possible further deployed stent. The image could then be processed and presented to the physician to indicate optimal or sub-optimal deployment. A graph for a stent diameter versus vessel wall diameter (as well as other parameters obtained from angiography while injecting contrast material, such as distance between stent (struts) and vessel wall, and area, length and volume of gap between the stent and vessel wall, etc.) can be analyzed. Such parameters and their analysis are known in the art and therefore is not expounded hereinbelow.

In order to prevent restenosis, i.e., re-narrowing or blockage of a blood vessel at the site of a previous angioplasty, the scoring mesh 13 or at least a part of it can comprise an active pharmacologic agent that can be delivered to a wall of the blood vessels scored or cut by the scoring mesh 13. A wide variety of active pharmacologic agents that can effectively inhibit inflammation and smooth-muscle cell growth are known. Examples of such pharmacologic agents include, but are not limited to, antiproliferative agents (e.g., Sirolimus and Paclitaxel drugs), immunomodulators, antithrombotics, and growth factor inhibitors.

The active pharmacologic agents may be provided on or within the scoring mesh 13 in a variety of ways. For example, the active agents may be coated over at least a portion of a surface of the filaments 131, typically by dipping, spraying, painting, plasma deposition, electroplating, ink jet coating, centrifuge systems or the like.

Likewise, the active substance may be incorporated in a coating including a polymeric carrier. Examples of suitable polymeric carriers include, but are not limited to those comprising polylactic acids (PLA), polyglycolic acids (PLG), collagens, and the like. Alternatively, the polymeric carrier may be a porous but non-resorbable material such as porous silicon or polyethylene. Hydrogels such as Poly Ethylene Oxide (PEO) may be used and release the drug through swelling and erosion. The polymer can coat the filaments 131 of the scoring mesh 13, or alternatively can create a film between at least some of the filaments 131 or any combination of the above.

Having explained the structure of the cutting balloon assembly of the present invention, a method of manufacturing the assembly and the scoring mesh 13 will be described hereinbelow. The method begins from providing a predetermined number of filaments having predetermined properties, predetermined diameter and length.

According to one embodiment, the manufacturing of the scoring mesh is carried out from one length of filament. According to another embodiment, the manufacturing of the scoring mesh is carried out from several filaments. Various types of filaments suitable for the scoring mesh 13 are described above.

Figure 3:
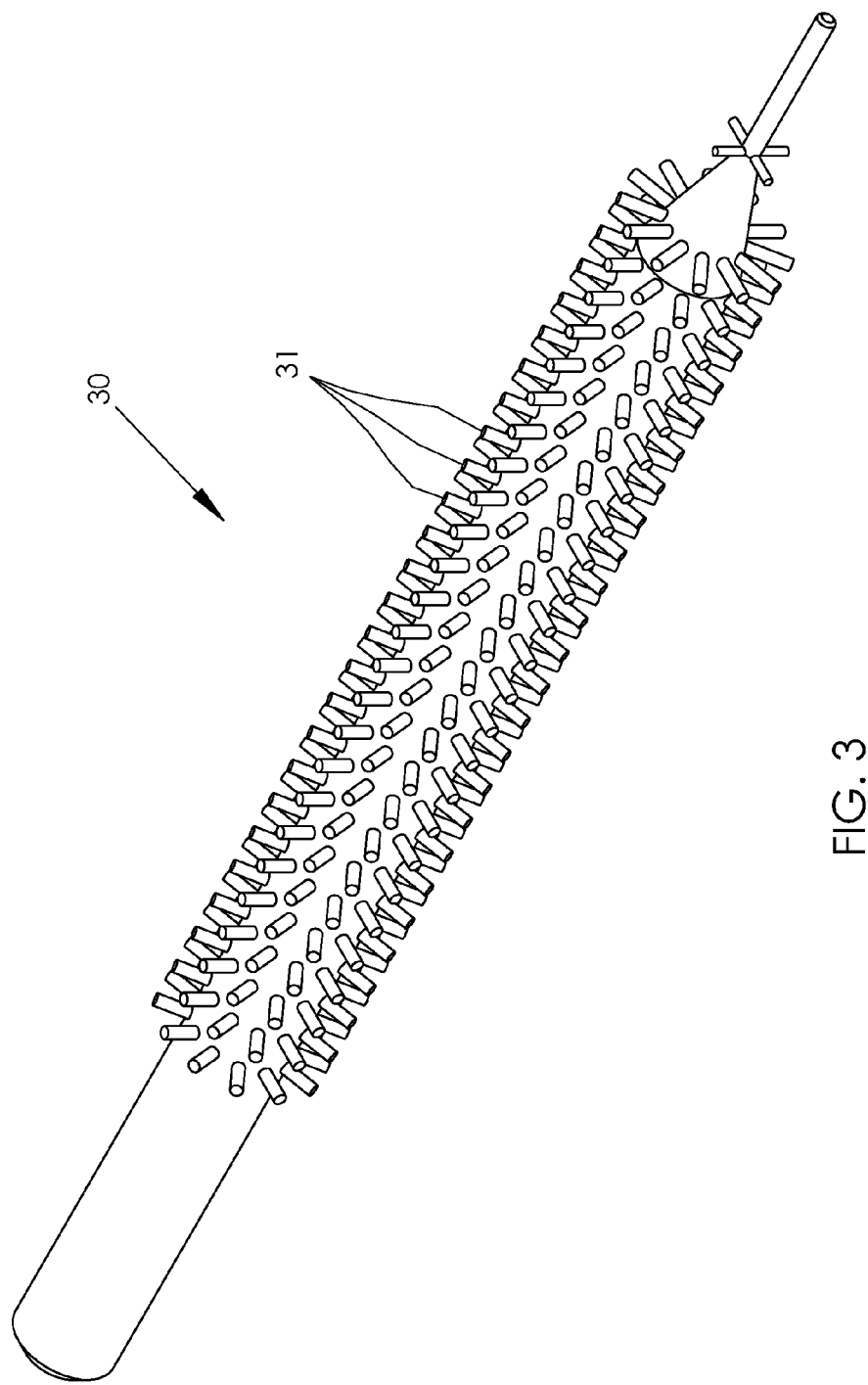
FIG. 3 shows a perspective view of an exemplary weaving jig suitable for preparation of the scoring mesh, according to one embodiment of the present invention.

After providing the filaments, the process for the fabrication of the cutting balloon assembly includes weaving the scoring mesh from one length of filament or from several filaments. According to one embodiment of the present invention, at least a part of the preparation of the scoring mesh is carried out on a weaving jig (mandrel). FIG. 3 shows a perspective view of an exemplary weaving jig 30 suitable for preparation of the scoring mesh of the present invention. The weaving jig 30 has a cylindrical structure including a plurality of pins 31 disposed circumferentially about the surface of the structure in rows and extending outwardly therefrom. Generally, a dimension of the jig is determined by the dimension of the expandable balloon and can be found either empirically or calculated taking into account the dimension of the balloon.

However, if a dimension of the balloon is relatively small, e.g., 0.5 mm-1 mm, then the dimension of the jig can be slightly greater than the dimension of the balloon, so it would be convenient a manual weaving of the mesh.

For example, a diameter of the weaving jig 30 can be in the range of 3 mm to 4 mm (millimeters), whereas a length of the jig 30 can, for example, be in the range of 30 mm to 40 mm. Each row of pins can, for example, include between 10 and 14 pins having a diameter of about 0.4 mm and a length of the protruded portion of about 2 mm. A number of the rows can, for example, be about 25, and a distance between the rows can be about 1.5 mm.

The method for fabrication of the scoring mesh of the present invention further includes interlacing the filaments of the scoring mesh on the jig 30. Specifically, the filaments are placed between the pins and interlaced to form a cross-hatched pattern. The interlacing includes interweaving the filaments by passing each of the filaments above one or more other filaments and under one or more other intersecting filaments, and intertwining a part of the filaments by twining one filament with another and/or twining one filament about another filament to form permanent links.

Figure 4A:
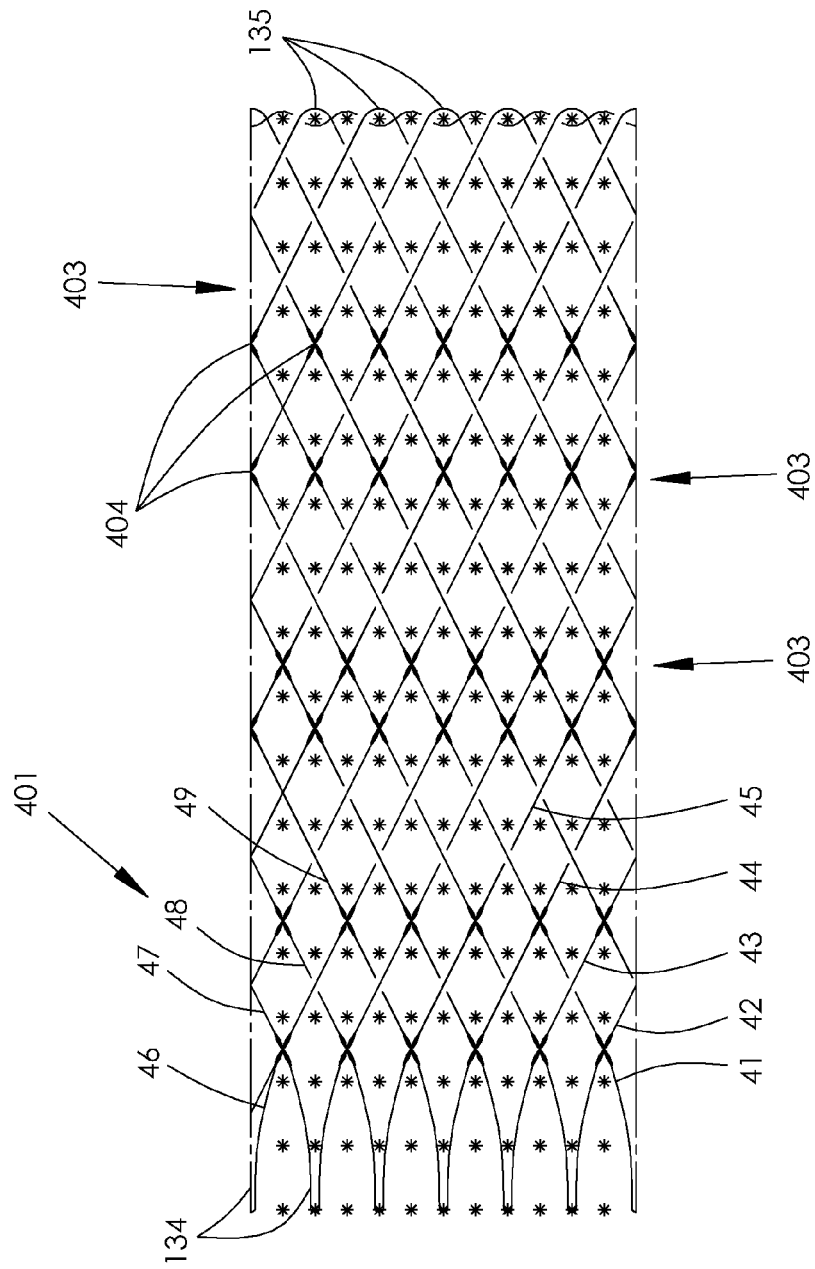

FIGS. 4A-4G show various embodiments of the pattern of the scoring mesh of the present invention. Specifically, FIG. 4A shows a pattern 401 in which each ascending wire filament interweaves with all descending filaments and vice versa. Moreover, a part of the filaments are intertwined together to form permanent links.

For example, an ascending (from a left end toward a right end) filament 41 goes first above a descending filament 42, then under a descending filament 43, then again above a descending filament 44, then again under a descending filament 45 and so on. On the other hand, a descending filament 46 goes first above an ascending filament 47, then under an ascending filament 48, then again above an ascending filament 49 and so on. The rest of the filaments are arranged similarly. As shown in FIG. 4A, a part of the interlacing filaments are twisted by one or more turns with intersecting filaments, and thereby form rows 403 of permanent links 404 with neighboring filaments. Such permanent links 404 can prevent slippage of the filaments away from their original contact points during exploitation of the scoring mesh. The rows 403 can have a predetermined periodicity along the length between the mesh proximal and distal ends, whereas the permanent links 404 can be arranged in predetermined places between the mesh proximal and distal ends and. This enables a control of a flexibility of the mesh for maintaining the mesh in the range of elastic deformations at stretching.

As shown in FIG. 4A, the interlacing filaments form filament loops 134 and 135 at the mesh ends.

The scoring mesh having the pattern 401 includes scoring elements which are formed by the turns of the twisted filaments forming the permanent contacts 404. These turns have a dimension that distinguishes from the dimension of a single wire filament, and thereby they have scoring properties.

It should be understood that when desired, dedicated scoring elements (not shown), e.g., ferrules with cutting edges, can be placed on the filaments. The scoring elements can, for example, be placed around the filaments forming the scoring mesh in points of intersection of the filaments; however, other locations on the filaments are also contemplated.

Figure 4B:
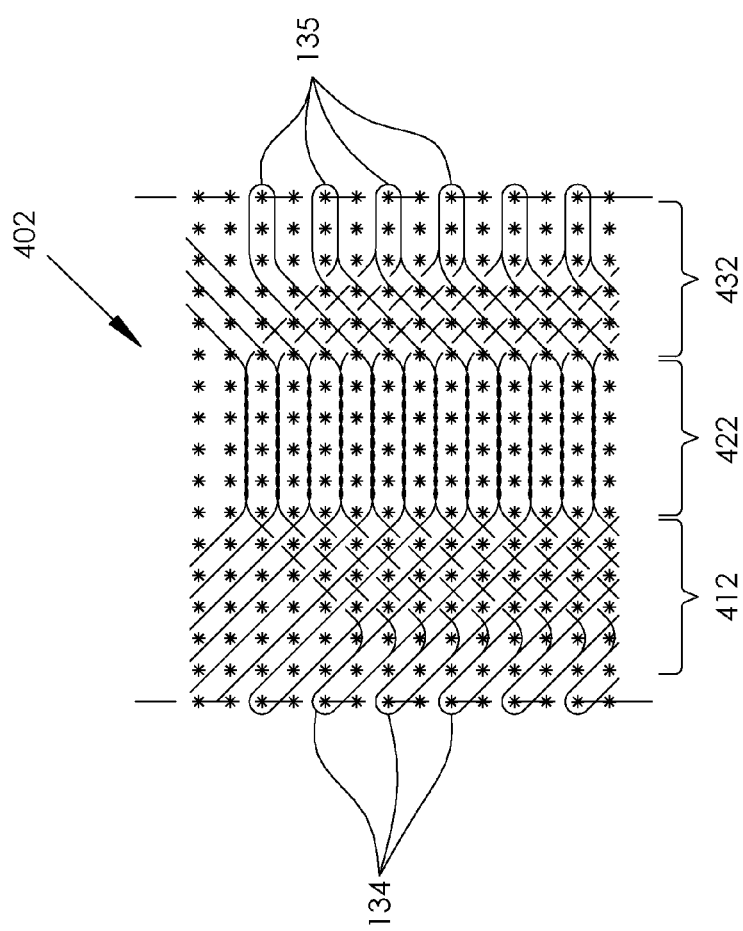

FIG. 4B shows a pattern 402 in which the interlacing wire filaments are interweaved in the vicinity of the mesh ends and are twisted in the middle region of the mesh by one or more turns, thereby forming permanent links in the middle region. Specifically, the wire filaments are interlaced in regions 412 and 432 near the mesh ends, in the manner shown in FIG. 4A, whereas in a region 422, each ascending (from the left end toward the right end) filament is twisted with one descending filament. At the mesh ends, the interlacing filaments form filament loops 134 and 135.

Figure 4C:
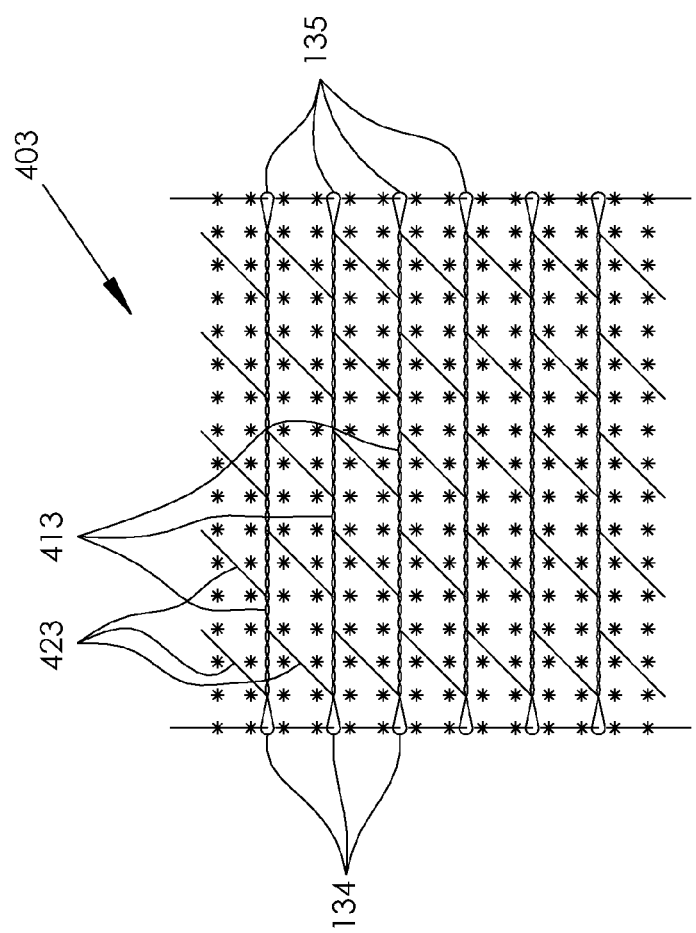

FIG. 4C shows a pattern 403 in which the mesh includes a plurality of self-twisted filament pairs 413 that are arranged in a parallel relationship to each other and extend from one mesh end towards another mesh end. At one or at both mesh ends, each of the self-twisted filaments forms filament loops 134 and 135. The self-twisted filament pairs 413 are interlaced by a plurality of intersecting filaments 423 that can intersect the self-twisted filament pairs 413 at various angles. The self-twisted filament pairs 413 can interweave and/or intertwine with the intersecting filaments 423. It should be noted that a mesh with such a pattern can withstand relatively large load during stretching deformations. Moreover, a flexibility of a mesh with such a pattern does not substantially differ in the flexibility of the pattern formed entirely from interweaved filaments, i.e. without intertwining. This feature is especially important in the case when a ratio between the diameter of the balloon in the inflated state and deflated state is relatively big, for example, 8:1 or more.

Figure 4D:
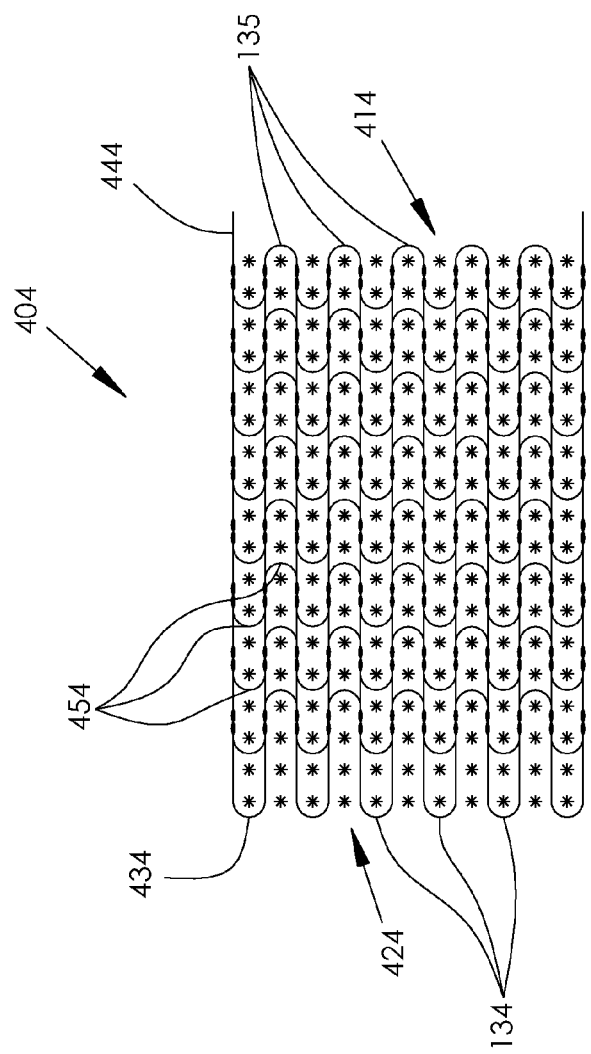

FIG. 4D shows a pattern 404 in which the mesh is formed from a filament 444 that extends from a mesh end 414 to another mesh end 424, where it forms a loop 434 and then returns to the original end 414. The meandering behavior of the filament 444 continues as required, thereby forming a plurality of the loops 134 and 135 at both mesh ends, correspondingly. The meandering filament 444 is interlaced by a plurality of intersecting filaments 454 which can be interweaved and/or twisted with the meandering filament 444.

Figure 4E:
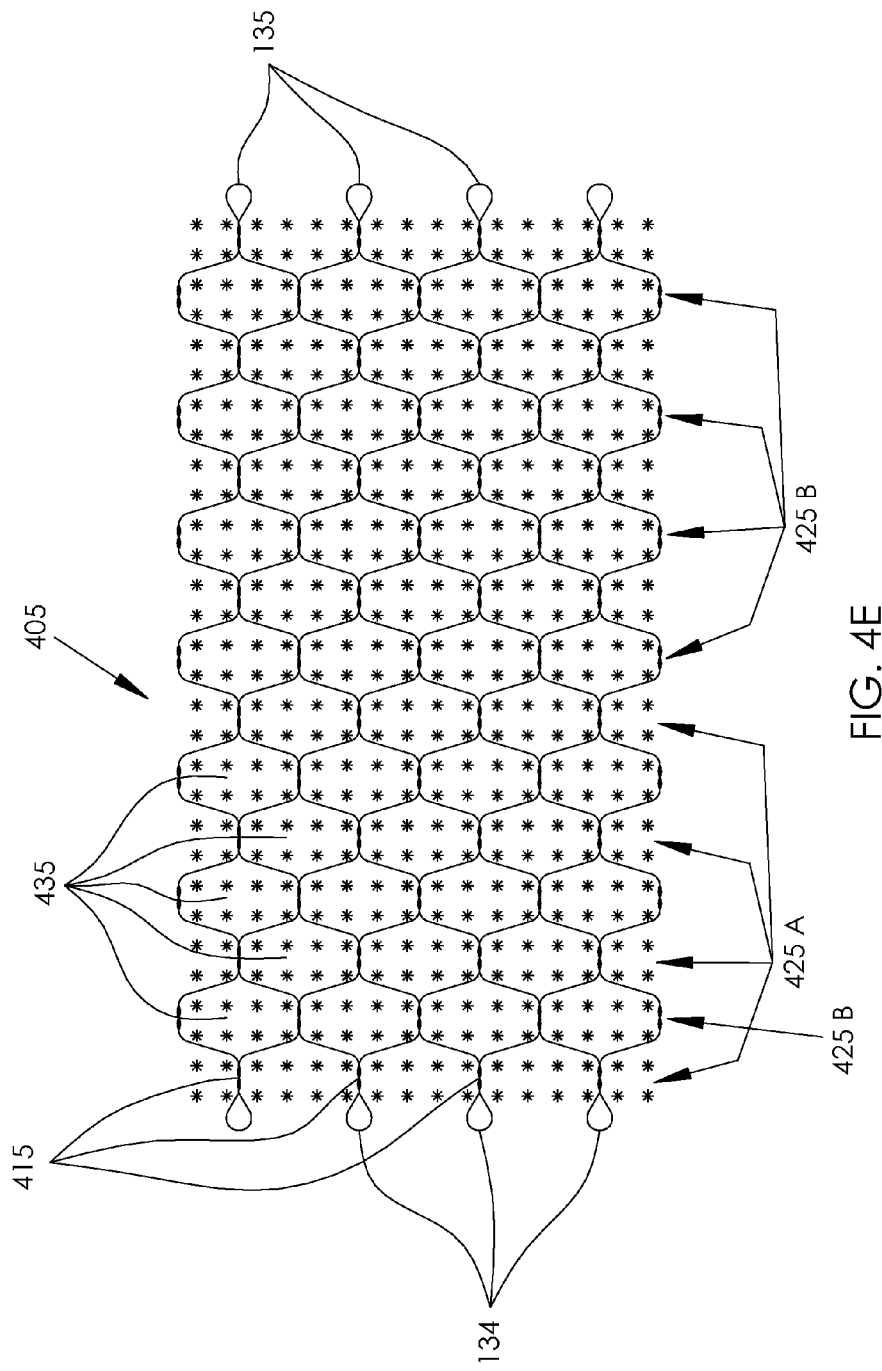

FIG. 4E shows a pattern 405 in which the mesh includes a plurality of filament pairs 415 that are arranged in a parallel relationship to each other and extend from one mesh end towards another mesh end. Filaments in the filament pairs 415 are self-twisted at twisted regions 425A. Furthermore, the filament pairs 415 ramify between the twisted regions 425A and form a region 425B of openings 435, and then converge back into the twisted regions 425A. As shown in FIG. 4E, in the region 425B of the opening 435, each filament of the filament pairs 415 is twisted by one or more turns with the filament of a neighboring filament pair. Each of the filament pairs forms filament loops 134 and 135 at one mesh end or at both mesh ends.

Figure 4F:
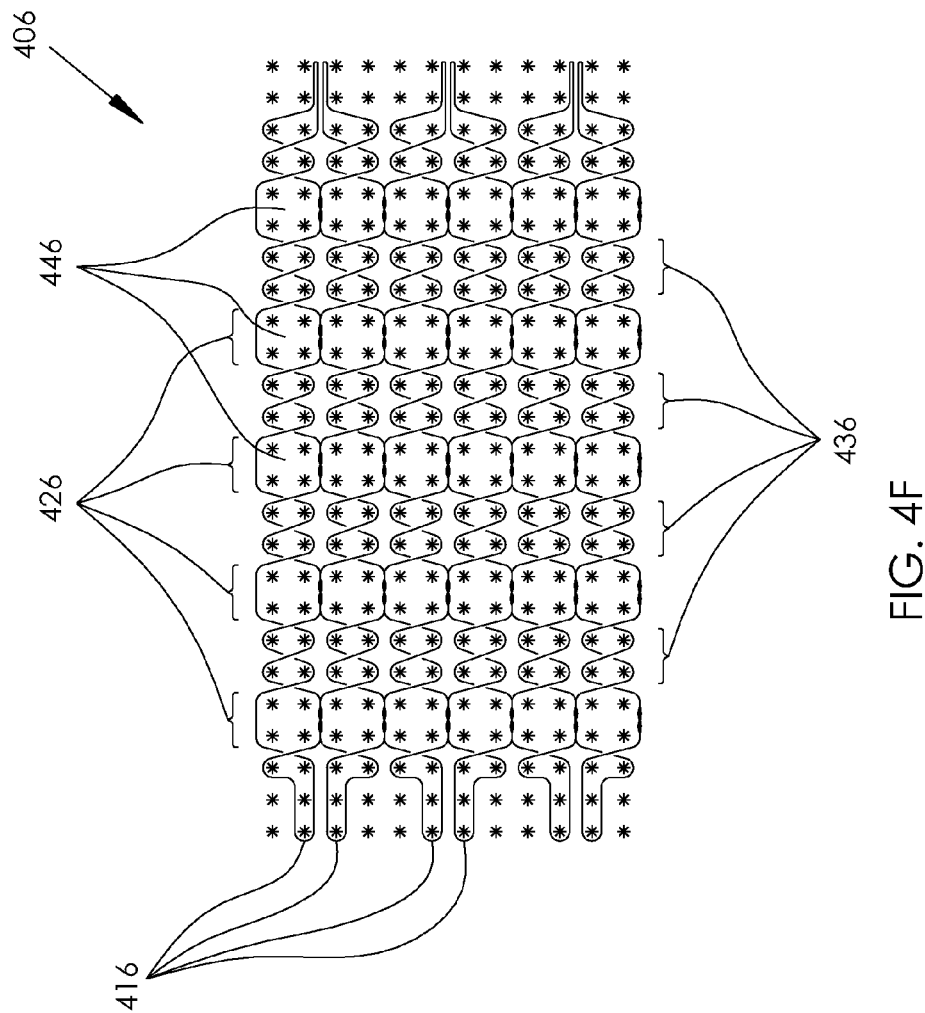

FIG. 4F shows a pattern 406 in which the mesh includes a plurality of filament pairs 416 that are arranged in a parallel relationship to each other and extend from one mesh end towards another mesh end. Filaments in the filament pairs 416 are arranged in regions of a first type 426 and a second type 436. The filaments in the regions of the first type 426 form openings 446, whereas the filaments in the regions of the second type 436 are self-interlaced in an 8-shaped form. As shown in FIG. 4F, in the opening 446, each filament of the filament pairs 416 is twisted by one or more turns with the filament of a neighboring filament pair. Each of the filament pairs 416 forms filament loops at one mesh end (as shown in FIG. 4F) or at both mesh ends.

When desired, the scoring mesh can be fabricated only on a part of the weaving surface of the jig (30 in FIG. 3). FIG. 4G shows a pattern 407 in which a mesh 457 includes two pairs of filaments 417 and 427 which are extended and self-interlaced between mesh ends 437 and 447. At the mesh ends 437 and 447, at least one of the filament pairs forms filament loops 134 and 135. When such a mesh is mounted on a balloon 51, it can be wound around the balloon 51 as a band, as shown in FIG. 5.

After weaving, the process of mesh fabrication further includes annealing of the scoring mesh for memorizing and storing the mesh shape and thereby imparting structural rigidity and dilatation ability to the mesh. The parameters of the annealing depend on the materials of the filaments and the method of heating. The annealing can be carried in one step or in a few steps with consequent heating and cooling the mesh.

According to one embodiment, the annealing of the scoring mesh is carried out in two stages. First, a preliminary annealing is carried on the jig (30 in FIG. 3). Such a preliminary annealing treatment can relieve the internal stresses in the material and provide memorization of the mesh shape. A diameter of the expandable balloon (12 in FIG. 1) in the deflated state can, for example, be in the range of about 0.5 mm-1 mm. Therefore, for convenience of the fabrication, a diameter of the cylindrical part of the jig can be greater than the diameter of the expandable balloon (12 in FIG. 1) in the deflated state.

After heating, the mesh, which is mounted on the jig, is cooled and taken off from the jig.

Then, the mesh having a dimension of the jig after the preliminary annealing is stretched up to a diameter that is usually less than the diameter of the balloon in the deflated state, e.g., to the diameter of about 0.1 mm-0.2 mm.

Further, the stretched mesh is put on a mandrel having a diameter less that than the diameter of the deflated balloon, and fastened to the mandrel by a string. The mandrel, can for example, be a piece of wire made of steel, nickel-titanium alloy or any other suitable material. The string can, for example, be made from copper, a copper alloy (e.g., Manganin™) or any other suitable material.

Then, a final annealing is carried out for the mesh placed on the mandrel to provide final memorization of the mesh shape. A dimension of such a mesh after the final annealing can be slightly less than the dimension of the deflated balloon so that the mesh, even with remaining deformations, would be tightly fitted to the balloon after deflation.

It should be appreciated that the invention is not limited to the specific implementation of the preliminary annealing and final annealing. According to one embodiment, the heating is carried out by placing the mesh mounted on the weaving jig in a furnace or consequently in various furnaces configured for this purpose. When the mesh is fabricated from a nickel-titanium alloy (e.g., Nitinol™), the preliminary annealing and the final annealing can, for example, be carried out at a temperature of about 400° C.-600° C. for at least about 10 min. After the heating, the mesh can be cooled to the room temperature. It should be understood that generally time of the thermal treatment may be shorter or longer than 10 minutes, depending on the heating technique, jig mass, etc.

According to another embodiment, the heating is carried out by passing a required electric current through the wire filaments that in this case should be made from at least partially electrically conducting material. For example, when the material of the mesh is Nitinol a current of about 1 A (Ampere) to 3 A applied for about 2 sec to tens of seconds can be used.

After the final annealing, the scoring mesh is mounted on the expandable balloon (12 in FIG. 1) of the cutting balloon assembly (10 in FIG. 1). The mounting includes placing the scoring mesh on the balloon and connecting the mesh to the ends of the expandable balloon 12 or to the delivery catheter 11 at one or more points, as described above with reference to FIG. 1.

As such, those skilled in the art to which the present invention pertains, can appreciate that while the present invention has been described in terms of preferred embodiments, the concept upon which this disclosure is based may readily be utilized as a basis for the designing of other structures and processes for carrying out the several purposes of the present invention.

It should be understood that the snare of the present invention is not limited to a medical treatment of a human body. It can be successfully employed for medical treatments of animals as well.

Also, it is to be understood that the phraseology and terminology employed herein are for the purpose of description and should not be regarded as limiting.

In the method claims that follow, alphabetic characters used to designate claim steps are provided for convenience only and do not imply any particular order of performing the steps.

It is important, therefore, that the scope of the invention is not construed as being limited by the illustrative embodiments set forth herein. Other variations are possible within the scope of the present invention as defined in the appended claims. Other combinations and sub-combinations of features, functions, elements and/or properties may be claimed through amendment of the present claims or presentation of new claims in this or a related application. Such amended or new claims, whether they are directed to different combinations or directed to the same combinations, whether different, broader, narrower or equal in scope to the original claims, are also regarded as included within the subject matter of the present description.

What is claimed is:

1. A cutting balloon assembly, comprising:
    a delivery catheter having a catheter proximal end, a catheter distal end, and at least one catheter lumen extending between the catheter proximal and distal ends;
    an expandable balloon having a balloon proximal end and a balloon distal end, the expandable balloon mounted on the catheter distal end; and
    a scoring mesh disposed around the expandable balloon, the scoring mesh having no self-expandable portions along an entire length of the scoring mesh, and comprising interlacing filaments that interweave between a mesh proximal end and a mesh distal end, at least one of the filaments interweaves between the mesh proximal end and the mesh distal end, protrudes from the mesh distal end, bends upon itself, arrives back at the distal end of the mesh to form a distal filament loop at the mesh distal end, and again interweaves between the mesh proximal end and the mesh distal end after forming the distal filament loop; at least one of the interlacing filaments interweaves between the mesh proximal end and the mesh distal end, protrudes from the mesh proximal end, bends upon itself, arrives back at the proximal end of the mesh to form a proximal filament loop at the mesh proximal end, and again interweaves between the mesh proximal end and the mesh distal end after forming the proximal filament loop; and at least one of the filaments intertwines with neighboring filaments to form permanent links arranged in rows being not evenly spaced over the entire length of the mesh, and at least a part of the rows being located on a cylindrical middle portion of the expandable balloon between two conical portions of the expandable balloon which are between the mesh proximal end and the mesh distal end, wherein
    the scoring mesh includes scoring elements corresponding to at least some of the permanent links on the cylindrical middle portion, the scoring elements having sharp edges that are configured to incise calcinated, fibrotic or other hard stenosed regions of vessel walls.

2. The cutting balloon assembly of claim 1, wherein the scoring mesh is connected to the balloon proximal and distal ends.

3. The cutting balloon assembly of claim 1, further comprising at least one distal string wound radially around the balloon distal end and woven through openings in the distal filament loop, connecting the distal filament loop of the scoring mesh to the balloon distal end.

4. The cutting balloon assembly of claim 1, further comprising at least one proximal string wound radially around the balloon proximal end and woven through the openings in the proximal filament loop, connecting the proximal filament loop of the scoring mesh to the balloon proximal end.

5. The cutting balloon assembly of claim 1, further comprising at least one distal string wound round the delivery catheter after the balloon distal end in relation to an operator using the cutting balloon assembly, said at least one distal string passes through the openings in the distal filaments loop, thereby to tie the scoring mesh to the delivery catheter.

6. The cutting balloon assembly of claim 1, further comprising at least one proximal string wound round the delivery catheter before the balloon proximal end in relation to an operator using the cutting balloon assembly, thereby to tie the filaments at the mesh proximal end to the delivery catheter.

7. The cutting balloon assembly of claim 1, wherein the scoring elements are formed by twisted turns of the intertwined filaments forming said at least one permanent link.

8. The cutting balloon assembly of claim 7, wherein said twisted turns of the intertwined filaments forming said at least one permanent link extend in a longitudinal direction of the balloon.

9. The cutting balloon assembly of claim 1, wherein the scoring elements are dedicated elements attached to or placed around the filaments forming the scoring mesh.

10. The cutting balloon assembly of claim 1, wherein the filaments of the scoring mesh are radiopaque.

11. The cutting balloon assembly of claim 10 configured for a simulation of an optimal position for deployment of a stent.

12. The cutting balloon assembly of claim 11, wherein the simulation comprises:
    advancing the balloon assembly, by using fluoroscopy, over a guidewire within a cardiovascular system of a patient so as to place the balloon adjacent a stenotic lesion inside a stenosed region;
    inflating the balloon; and
    taking angiograms of the radiopaque scoring mesh.

13. The cutting balloon assembly of claim 12, wherein the simulation further comprises processing and analyzing an image of the radiopaque scoring mesh on the angiograms so as to obtain the optimal position for deployment of the stent.

14. The cutting balloon assembly of claim 1, wherein at least a part of the scoring mesh comprises an active pharmacological agent that can inhibit inflammation and smooth-muscle cell growth.

15. The cutting balloon assembly of claim 1, further comprising a guiding catheter including a lumen for housing the delivery catheter.

16. The cutting balloon assembly of claim 1, further comprising at least one guide wire.

17. The cutting balloon assembly of claim 1, wherein the permanent links are arranged in rows having a predetermined periodicity along the length between the mesh proximal and distal ends.

18. The cutting balloon assembly of claim 1, wherein at least one of the rows of the permanent links is separated from an adjacent row of the rows of permanent links by a row of intersections of filaments that interweave, the intersections of filaments that interweave not forming permanent links.

19. A cutting balloon assembly, comprising:
a delivery catheter having a catheter proximal end, a catheter distal end, and at least one catheter lumen extending between the catheter proximal and distal ends;
an expandable balloon having a balloon proximal end and a balloon distal end, the expandable balloon mounted on the catheter distal end; and
a scoring mesh disposed around the expandable balloon, the scoring mesh having no self-expandable portions along an entire length of the scoring mesh, and comprising one continuous and monolithic length of wire that is woven to form interlacing portions that interweave between a mesh proximal end and a mesh distal end, at least one portion of the one continuous and monolithic length of wire protrudes from the mesh distal end, bends upon itself and arrives back at the distal end of the mesh to form distal filament loops at the mesh distal end; at least one portion of the one continuous and monolithic length of wire protrudes from the mesh proximal end, bends upon itself and arrives back at the proximal end of the mesh to form proximal filament loops at the mesh proximal end; and at least one of the interlacing portions intertwines with neighboring interlacing portions to form permanent links arranged in rows being not evenly spaced over the entire length of the mesh, and at least a part of the rows being located on a cylindrical middle portion of the expandable balloon between two conical portions of the expandable balloon which are between the mesh proximal end and the mesh distal end, wherein
the scoring mesh includes scoring elements corresponding to at least some of the permanent links on the cylindrical middle portion, the scoring elements having sharp edges that are configured to incise calcinated, fibrotic or other hard stenosed regions of vessel walls.

20. A cutting balloon assembly, comprising:
a delivery catheter having a catheter proximal end, a catheter distal end, and at least one catheter lumen extending between the catheter proximal and distal ends;
an expandable balloon having a balloon proximal end and a balloon distal end, the expandable balloon mounted on the catheter distal end; and
a scoring mesh disposed around the expandable balloon, the scoring mesh not having self-expandable portions along an entire length of the scoring mesh, and comprising interlacing filaments that interweave between a mesh proximal end and a mesh distal end, at least one of the filaments interweaves between the mesh proximal end and the mesh distal end, protrudes from the mesh distal end, bends upon itself, arrives back at the distal end of the mesh to form a distal filament loop at the mesh distal end, and again interweaves between the mesh proximal end and the mesh distal end after forming the distal filament loop; at least one of the interlacing filaments interweaves between the mesh proximal end and the mesh distal end, protrudes from the mesh proximal end, bends upon itself, arrives back at the proximal end of the mesh to form a proximal filament loop at the mesh proximal and again interweaves between the mesh proximal end and the mesh distal end after forming the proximal filament loop; and at least one of the filaments intertwines with neighboring filaments to form permanent links arranged in rows being not evenly spaced over the entire length of the mesh, and at least a part of the rows being located on a cylindrical middle portion of the expandable balloon between two conical portions of the expandable balloon which are between the mesh proximal end and the mesh distal end, wherein
the scoring mesh corresponding to at least some of the permanent links on the cylindrical middle portion, the scoring elements, the scoring mesh including dedicated scoring elements that are attached to at least a portion of one or more of the filaments at positions other than crossing points of the one or more filaments and that have sharp edges that are configured to incise calcinated, fibrotic or other hard stenosed regions of vessel walls.

21. A cutting balloon assembly, comprising:
a delivery catheter having a catheter proximal end, a catheter distal end, and at least one catheter lumen extending between the catheter proximal and distal ends;
an expandable balloon having a balloon proximal end and a balloon distal end, the expandable balloon mounted on the catheter distal end; and
a scoring mesh disposed around the expandable balloon, the scoring mesh having no self-expandable portions along an entire length of the scoring mesh, and comprising interlacing filaments that interweave between a mesh proximal end and a mesh distal end, at least one of the filaments interweaves between the mesh proximal end and the mesh distal end, protrudes from the mesh distal end, bends upon itself, arrives back at the distal end of the mesh to form a distal filament loop at the mesh distal and again interweaves between the mesh proximal end and the mesh distal end after forming the distal filament loop; at least one of the interlacing filaments interweaves between the mesh proximal end and the mesh distal end, protrudes from the mesh proximal end, bends upon itself, arrives back at the proximal end of the mesh to form a proximal filament loop at the mesh proximal and again interweaves between the mesh proximal end and the mesh distal end after forming the proximal filament loop; and at least one of the filaments intertwines with neighboring filaments to form permanent links arranged in rows being not evenly spaced over the entire length of the mesh, and at least a part of the rows being located on a cylindrical middle portion of the expandable balloon between two conical portions of the expandable balloon which are between the mesh proximal end and the mesh distal end, wherein
the scoring mesh includes scoring elements corresponding to at least some of the permanent links on the cylindrical middle portion, the scoring elements having sharp edges that are configured to incise calcinated, fibrotic or other hard stenosed regions of vessel walls, and the scoring elements are connected to both the proximal filament loop and the distal filament loop.

\* \* \* \* \*